(12) United States Patent
Yu et al.

(10) Patent No.: US 10,434,196 B2
(45) Date of Patent: Oct. 8, 2019

(54) MULTIVALENT SACCHARIDE COMPLEX, RADIOACTIVE MULTIVALENT SACCHARIDE COMPLEX CONTRAST AGENT, AND USE THEREOF

(71) Applicant: Institute of Nuclear Energy Research, Atomic Energy Council, Executive Yuan, R.O.C, Taoyuan (TW)

(72) Inventors: Hung-Man Yu, Taoyuan (TW); Wuu-Jyh Lin, Taoyuan (TW); Mei-Hui Wang, Taoyuan (TW); Chun-Hao Tseng, Taoyuan (TW)

(73) Assignee: INSTITUTE OF NUCLEAR ENERGY RESEARCH, ATOMIC ENERGY COUNCIL, EXECUTIVE YUAN, R.O.C, Taoyuan (TW)

( * ) Notice: Subject to any disclaimer, the term of this patent is extended or adjusted under 35 U.S.C. 154(b) by 0 days.

(21) Appl. No.: 15/887,045

(22) Filed: Feb. 2, 2018

(65) Prior Publication Data

US 2019/0091352 A1    Mar. 28, 2019

(30) Foreign Application Priority Data

Sep. 22, 2017 (TW) .............................. 106132629 A

(51) Int. Cl.
  *A61K 51/04* (2006.01)
  *C07H 23/00* (2006.01)

(52) U.S. Cl.
  CPC ...... *A61K 51/0491* (2013.01); *A61K 51/0497* (2013.01); *C07H 23/00* (2013.01); *A61K 2123/00* (2013.01)

(58) Field of Classification Search
  CPC ............................... A61K 51/00; C07H 23/00
  See application file for complete search history.

(56) References Cited

U.S. PATENT DOCUMENTS

2009/0087377 A1* 4/2009 Azhdarinia ........ A61K 51/0482
                                                              424/1.65

* cited by examiner

*Primary Examiner* — Michael G. Hartley
*Assistant Examiner* — Jagadishwar R Samala
(74) *Attorney, Agent, or Firm* — Locke Lord LLP; Tim Tingkang Xia, Esq.

(57) ABSTRACT

Disclosed herein are a multivalent saccharide complex, a radioactive multivalent saccharide complex contrast agent and use thereof. The multivalent saccharide complex has a chelator, a linker, and glucose, and is configured to diagnose and evaluate the therapeutic effect of cancers.

9 Claims, 9 Drawing Sheets

MULTIVALENT SACCHARIDE COMPLEX, RADIOACTIVE MULTIVALENT SACCHARIDE COMPLEX CONTRAST AGENT, AND USE THEREOF

CROSS-REFERENCE TO RELATED APPLICATION

This application also claims priority to Taiwan Patent Application No. 106132629 filed in the Taiwan Patent Office on Sep. 22, 2017, the entire content of which is incorporated herein by reference.

TECHNICAL FIELD

The present disclosure relates to the technical field of medical imaging, and more particularly to a multivalent saccharide complex for imaging therewith.

BACKGROUND

Malignant tumors are the world's major public health issue and the second leading cause of morbidity in the United States. It is estimated in the American Cancer Society's Annual Cancer Report of 2017 that there will be 1,688,780 new cancer cases and 600,920 cancer deaths in the United States in 2017. It means that about 1,650 deaths occur daily. Moreover, the National Health Department, Taiwan Ministry of Health and Welfare released the latest list of the top ten cancers in May, 2017, showing that the number of patients with cancers and the rate of incidence grow increasingly in Taiwan, and malignant tumors have always been the first leading cause of morbidity for the consecutive 34 years. However, early diagnosis of cancers and proper early treatments of the patients can greatly improve the survival rate. For example, if patients with colorectal cancer and breast cancer are given appropriate treatment in the early stage of cancers, the prognosis of the patients is usually good.

The glucose analogue $^{18}$F-FDG (2-Deoxy-2-fluoro-D-glucose) commonly used in clinic at present suffers from many restrictions during the use. For example, $^{18}$F-FDG is difficult to be prepared, and the process requires the use of a cyclotron to produce F-18. However, such an apparatus is highly expensive, and not a usual basic apparatus equipped in a hospital. Moreover, a synthesis kit is necessitated during the preparation of $^{18}$F-FDG, and $^{18}$F-FDG can be obtained only after the steps of water removal, fluorination, deprotection, and others, so the synthesis time is long. Furthermore, $^{18}$F-FDG is absorbed in all the tissues or organs that metabolize glucose in an organism, resulting in a very high background value in the brain and heart. This makes it difficult to distinguish the normal tissue from the tumor using $^{18}$F-FDG imaging in these organs and their surrounding tissues, such that $^{18}$F-FDG has limitations in detection therewith. Moreover, the $^{18}$F-FDG uptake is also high in an inflammatory tissue, so the tumor is also difficult to be distinguished from the inflammatory tissue. It can be seen that the preparation of $^{18}$F-FDG is complex and time consuming, and the specificity is low. In view of this, there is an urgent need in the art for an improved multivalent saccharide complex, to overcome the defects existing in the prior art.

SUMMARY

To facilitate the understanding of the fundamental meaning of the present disclosure, brief description of the present disclosure is provided in the summary, which is not a complete description of the present disclosure and not intended to define the technical features or scope of the present invention.

An aspect of the present disclosure relates to a multivalent saccharide complex, which comprises a chelator and at least two molecules of glucose attached to the chelator respectively through a linker. In an optional embodiment, the chelator may be 1,4,7-triazacyclononane-N,N',N"-triacetic acid (NOTA), 1,4,7,10-tetraazacyclododecane-1,4,7,10-tetraacetic acid (DOTA), di ethylenetriaminepentaacetic acid (DTPA), 1,4,8,11-tetraaz acyclotetradecane-N,N',N",N"'-tetraacetic acid (TETA), or 1,4,7-triazacyclononane phosphinic acid (TRAP). The linker may be polyethylene glycol (PEG), an amino acid or a peptide.

An aspect of the present disclosure relates to a multivalent saccharide complex, which has a structure of Formula (1):

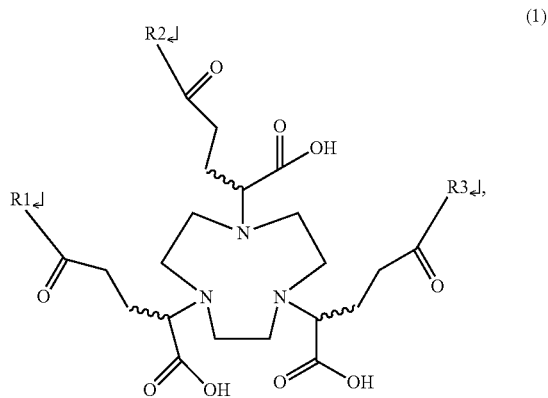

(1)

in which any two functional groups of R1, R2, and R3 are glucose, and the other functional group is hydrogen. Also, the wavy lines "〜〜〜" as shown in formula (1) are linker molecules, wherein the linker is polyethylene glycol (PEG), an amino acid or a peptide.

According to an embodiment of the present disclosure, in the multivalent saccharide complex of chemical Formula (1), R1, R2 and R3 are all glucose.

According to another embodiment of the present disclosure, the multivalent saccharide complex further comprises a radioactive isotope labeled on the compound of Formula (1). In an optional embodiment, the radioactive isotope may be rhenium-188, technetium-99 m, indium-111, lutetium-177, gallium-68, yttrium 90, flurine-18, or copper-64.

In a specific embodiment, the radioactive isotope is gallium-68.

Another aspect of the present invention relates to a contrast agent. The contrast agent comprises a multivalent saccharide complex according to any one of the above embodiments and an excipient acceptable in the contrast agent.

A further aspect of the present invention relates to use of the multivalent saccharide complex in the preparation of pharmaceutical products for diagnosing cancers.

In an optional embodiment, the cancers are selected from the group consisting of lymphoma, multiple myeloma, testicular cancer, thyroid cancer, prostate cancer, throat cancer, cervix cancer, nasopharyngeal carcinoma, breast cancer, colorectal cancer, pancreatic cancer, gastric cancer, head and neck cancer, esophageal cancer, rectal cancer, bladder cancer, kidney cancer, lung cancer, liver cancer, brain cancer, melanoma, and skin cancer.

The central concept, the technical means employed and the various implementations of the present invention can be fully understood by those of ordinary skill in the art from reading the following embodiments.

BRIEF DESCRIPTION OF DRAWINGS

The foregoing and other objects, features, advantages and embodiments of the present invention will become more apparent from the following brief description of drawings, in which.

DETAILED DESCRIPTION OF DISCLOSED EMBODIMENTS

Figure 1A:
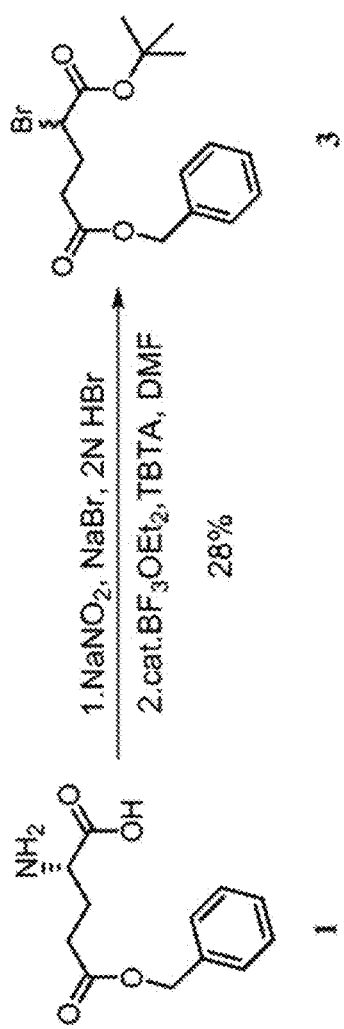
FIGS. 1A to 1E show a scheme for synthesizing a multivalent saccharide complex according to an embodiment of the present invention.

To make the description of the present disclosure more elaborate and complete, the implementations and specific embodiments of the present invention will be described in further detail hereinafter; however, the implementations and specific embodiments of the present invention are not limited thereto.

Unless otherwise indicated, the scientific and technical terms used herein have the same meanings as those understood by those of ordinary skill in the art. Moreover, the terms used herein cover the singular and plural referents, unless otherwise specified.

The term "subject" or "patient" refers to an animal that is capable of receiving the thermosensitive carrier of the present invention. In a preferred embodiment, the animal is a mammal, and in particular human.

The "cancer" may be a non-solid tumor or a solid tumor. For example, the cancer may include, but is not limited to lymphoma, multiple myeloma, testicular cancer, thyroid cancer, prostate cancer, throat cancer, cervix cancer, nasopharyngeal carcinoma, breast cancer, colorectal cancer, pancreatic cancer, gastric cancer, head and neck cancer, esophageal cancer, rectal cancer, bladder cancer, kidney cancer, lung cancer, liver cancer, brain cancer, melanoma, and skin cancer.

As used herein, the term "about" usually means that the actual value is within 10%, 5%, 1%, or 0.5% of a particular value or range, and that the actual value is within the acceptable standard error of the mean value, depending on the considerations of those of ordinary skill in the art to which this present invention pertains. Besides the experimental examples, or unless otherwise expressly stated, the ranges, the amounts, the values and the percentages used herein are modified with "about." Therefore, unless otherwise stated, the values or parameters disclosed in this specification and the appended claims are all approximate values and may vary depending on the requirements.

To solve the problems existing in the prior art, the present inventors initially propose a multivalent saccharide complex herein, which is a compound mainly having a structure of Formula (1):

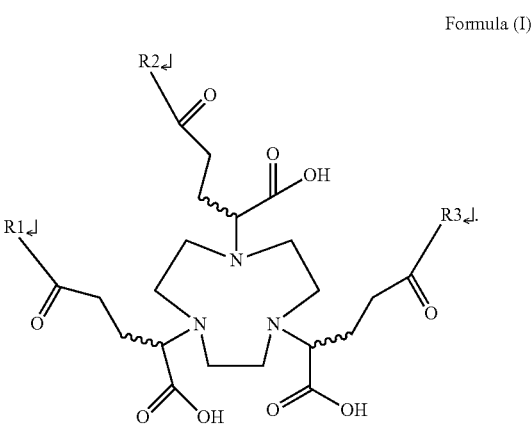

Formula (I)

The multivalent saccharide complex of the present invention is modified with a saccharide molecule at any two functional groups of R1, R2, and R3, in which the saccharide molecule is preferably glucose. Also, the wavy lines "〜〜" as shown in formula (1) are linker molecules, and the linker is polyethylene glycol (PEG), an amino acid or a peptide. The multivalent saccharide complex contrast agent of the present invention can quickly enter the tumor cells, enhance the signal contrast between the tumor and the surrounding normal tissue, and increase the detection efficiency. In addition to the use in the detection of malignant tumors, the multivalent saccharide complex contrast agent is also useful in the evaluation of the therapeutic effect of cancers by evaluating the appropriateness of treatment in a non-invasive way.

According to an experimental example of the present invention, the multivalent saccharide complex of the present invention has a molecular weight that is greater than that of $^{18}$F-FDG, and an uptake in normal brain and heart that is obviously lower than that of $^{18}$F-FDG. Therefore, compared with $^{18}$F-FDG, radioimaging (i.e., positron emission tomography (PET) scanning) using the multivalent saccharide complex of the present invention can enhance the signal contrast between the tumor and the surrounding normal tissue since the background values in the brain and lung of an individual are lower, thereby dramatically improving the detection efficiency.

Further, according to another embodiment of the present invention, to facilitate the clinical use, the time to label a radioactive isotope is shortened and the conventional complex steps are simplified. The saccharide complex of the present invention can be labeled with radioisotope gallium-68 (Ga-68) for radioimaging. Further, based on the results of the experimental examples, it is found that the multivalent saccharide complex of the present invention is significantly accumulated in tumor sites in the test animals with a tumor/muscle ratio of 5.1, indicating that the tumor is able to effectively take in the saccharide complex labeled with gallium-68 ($^{68}$Ga-NOTA-G3) of the present invention.

Various embodiments are disclosed herein below to explain various implementations of the present invention, so that the technical contents disclosed herein can be implemented by those of ordinary skill in the art according to the disclosure of the present specification. Therefore, the following examples are not intended to limit the scope of the claims of the present invention, and all references cited in this specification are deemed to be fully incorporated by reference as part of this specification.

EXAMPLE 1

Synthesis of the Multivalent Saccharide Complex of the Present Invention 1.1. Synthesis of NOTA-G3

1.1.1. Preparation of Compound 3

Referring to FIG. 1A, NaBr (4.5 g) and 1N HBr (30 ml) were added slowly to Compound 1 (3 g, 12.64 mmol) in an ice bath. $NaNO_2$ (1.6 g) was added batchwise in a fume hood since a large amount of gaseous bromine was produced upon the addition of $NaNO_2$, and reacted for 2 hrs at 0° C. The reaction was terminated, extracted with water and ethyl acetate, and concentrated to afford a yellow oil. The reaction was repeated four times. The collected crude product was separated by column chromatography eluting with ethyl acetate/n-hexane (1:4), and collected to obtain Compound 2 (5.2 g) (not shown) as a yellow oil (yield 34%). $^1$H NMR (300 MHz, $CDCl_3$) δ 7.36 (5 H, m, Ar), 5.14 (2H, s, $CH_2$-Ph), 4.40 (1H, dd, J=6, 9 Hz, CHBr), 2.63-2.31 (4H, m);$^{13}$C NMR (75 MHz, $CDCl_3$) δ 174.22, 172.38, 135.67, 128.79, 128.57, 128.45, 66.91, 44.52, 32.63, 29.64. Compound 2 (5.2 g, 17.27 mmol) was dissolved in dichloromethane (35 ml) in an ice bath. TBTA (8 g, 37 mmol) was dissolved in n-hexane (22 ml), and then the solution of TBTA in n-hexane was slowly added to the reaction mixture in an ice bath, to produce a white precipitate. DMF (1-3 ml) was added to dissolve the precipitate completely. A catalytic amount of boron trifluoride-ether complex (518 μl) was added to the reaction in an ice bath, naturally warmed to room temperature, and reacted for 2 days. The reaction was terminated, removed of most of the solvent, extracted with n-hexane and water, and then separated by column chromatography eluting with ethyl acetate/n-hexane (1:20). A product as a yellow oil (Compound 3) (4.2 g, yield 68%) was collected. 1H NMR (300 MHz, CDCl3) δ 7.36-7.34 (5H, m, Ar), 5.13 (2H, s, CH2-Ph), 4.24 (1H, dd, J=6, 9 Hz, CHBr), 2.55-2.52 (2H, m, CH2COOBn), 2.29-2.26 (2H, m, CHBr—CH2-CH2), 1.46 (9H, s);13C NMR (75 MHz, CDCl3) δ 172.13, 168.45, 135.86, 128.76, 128.49, 128.39, 82.79, 66.70, 46.80, 31.78, 29.87, 28.11.

1.1.2. Preparation of Compound 10

Figure 1B:
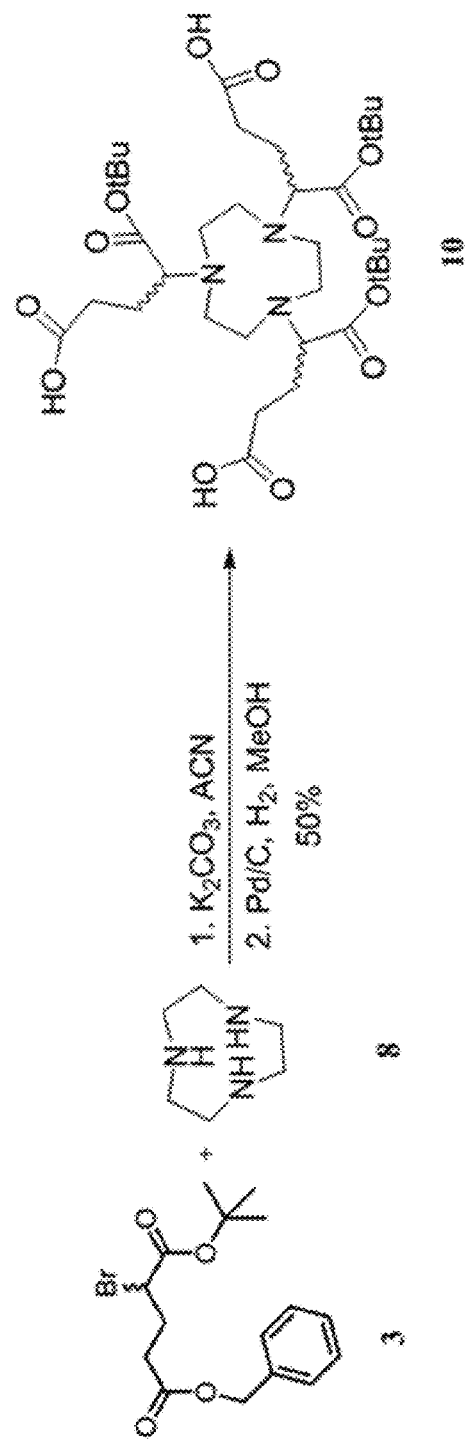

Referring to FIG. 1B, TACN hydrochloride (Compound 8, 30 mg, 0.125 mmol), Compound 3 (180 mg, 0.5 mmol) and potassium carbonate (400 mg) were dissolved in acetonitrile (8 ml), and reacted for 3 days at room temperature. After separation by column chromatography eluting with dichloromethane, and methanol/dichloromethane 1:20, to obtain Compound 9 (not shown) (about 80 mg, yield 66%). $^1$H NMR (300 MHz, $CDCl_3$) δ 7.36-7.27 (15 H, m, Ar), 5.10 (6H, s, $CH_2$-Ph), 3.11 (3H, t, J=7.8 Hz), 2.88-2.44 (18H, m), 1.99-1.84 (6H, m), 1.48 (27H, s). ESI-MS, m/z: 958.54 $[M+H]^+$, Found 958.20. Compound 9 (280 mg, 0.29 mmol) and 10% Pd/C (300 mg) were dissolved in 45 ml methanol/5 ml water, and reacted for 8-10 hrs at room temperature. The reaction was terminated, and removed of the solvent, to obtain Compound 10 (about 100 mg, yield 50%). 1H NMR (300 MHz, CD3OD) δ 3.8-3.6 (3H, m), 3.67-3.62 (12H, m), 2.46-2.44 (6H, m), 2.20-2.07 (6H, m), 1.50 (27H).

1.1.3. Preparation of Compound 18

Figure 1C:
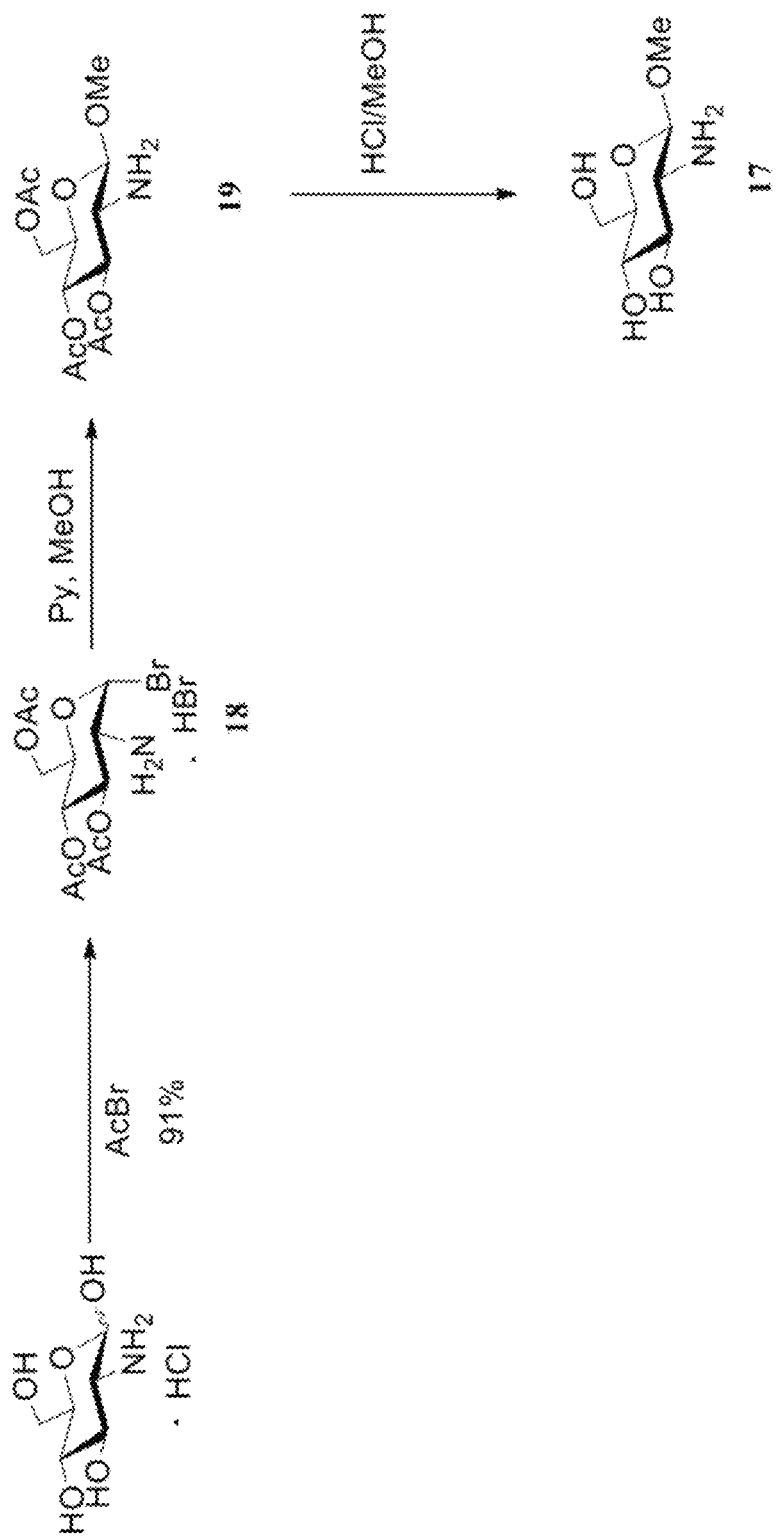

Referring to FIG. 1C, glucosamine hydrochloride (5 g, 23.18 mmol) was added slowly to acetyl bromide (20 ml) in an ice bath, warmed to room temperature, and stirred for three days. The solvent was removed, dichloromethane (100 ml) was added and then a solid was produced. The solid was removed, and the filtrate was collected. Ether was added and stood to produce a precipitate. The precipitate was filtered and washed to obtain a white solid, which was dried to obtain Compound 18 (9.5 g, yield 91%). 1H NMR (300 MHz, CDCl3) δ 8.64 (2 H, s, br), 7.08 (1H, d, J=3 Hz), 5.47 (1H, t, J=12 Hz), 5.21 (1H, t, J=12 Hz), 4.35-4.11 (3H, m), 3.8-3.9 (1H, m), 2.23-2.05 (9H, m);13C NMR (75 MHz, CDCl3) δ 172.13, 171.03, 169.75, 85.97, 73.45, 70.46, 67.23, 61.31, 54.81, 22.39, 21.25, 21.06.

1.1.4. Preparation of Compound 19

Referring to FIG. 1C, Compound 18 (5 g, 11.16 mmol), methanol (150 ml), and pyridine (3 ml) were reacted for 6-8 hrs at room temperature. The solvent was removed, the residue was extracted several times with dichloromethane, and an aqueous saturated sodium bicarbonate solution. The organic layer was concentrated and dried to obtain Compound 19 as a white solid (2.4 g, yield 67%). 1H NMR (300 MHz, DMSO-d6) δ 4.90 (1H, t, J=9 Hz), 4.75 (1H, t, J=9 Hz), 4.26 (1H, d, J=9 Hz), 4.20-4.14 (1H, dd), 4.00-3.99 (1H, dd), 3.80-3.70 (1H, m), 2.59-2.49 (1H, dd), 1.99-1.94 (9H);13C NMR (75 MHz, DMSO-d6) δ 170.21, 170.08, 169.55, 104.40, 74.82, 70.69, 68.92, 62.05, 56.51, 55.94, 20.72, 20.60, 20.51.

1.1.5. Preparation of Compound 17

Referring to FIG. 1C, Compound 19 (2.4 g) was slowly added to a mixture of acteyl chloride (20 ml) and methanol (100 ml) in an ice bath, warmed to room temperature, and reacted for 24 hrs. Then, the reaction was terminated.

1.1.6. Preparation of Compound 21

Figure 1D:
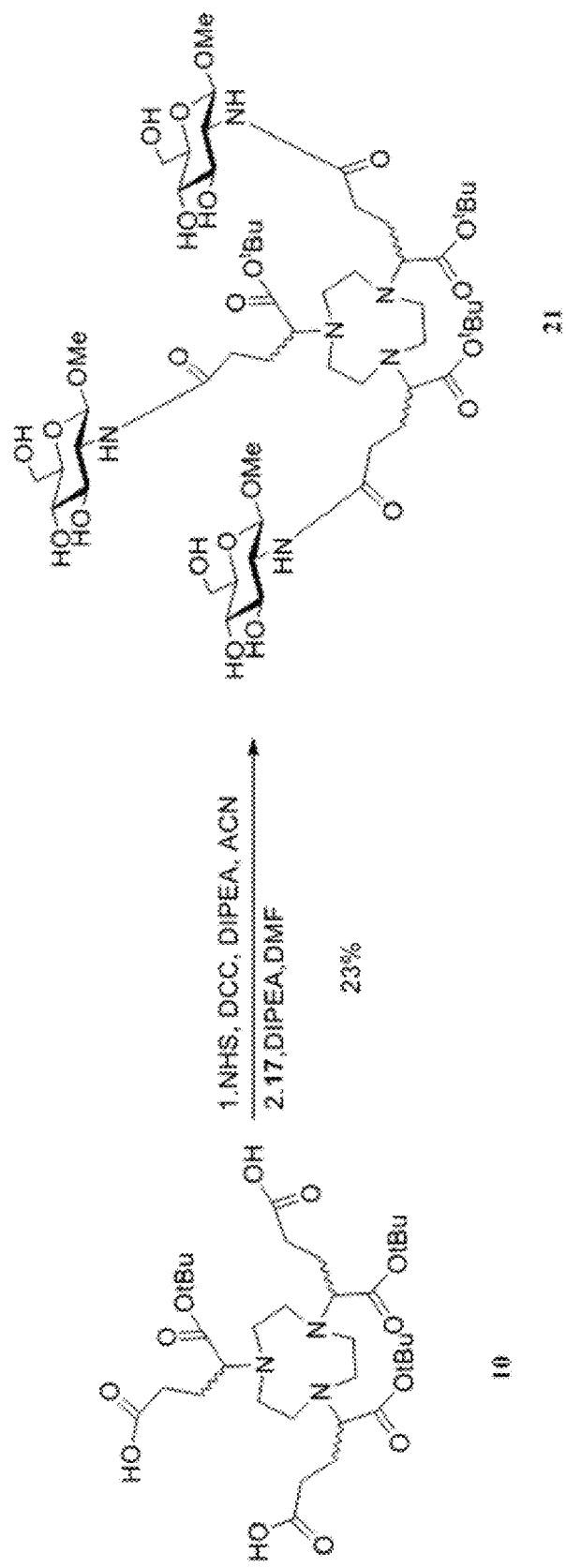

Referring to FIG. 1D, Compound 10 (about 120 mg), NHS (80 mg), DIPEA (800 μl) and DCC (150 mg) were dissolved in acetonitrile (4-5 ml), and reacted for 24 hrs at room temperature. The reaction was terminated. The white solid DCU was removed, dried under suction, directly dissolved together with Compound 17 (200 mg) and DIPEA (600 μl) in DMF (6 ml), and reacted. The reaction was stirred for two days and then terminated. Ether was added and a white precipitate was produced. The crude product was separated by reverse phase column chromatography, to obtain Compound 21 (50 mg, yield 23%). ESI-MS, m/z: 1213.65 [M+H]+, Found 1213.50.

Preparation of Compound 22

Figure 1E:
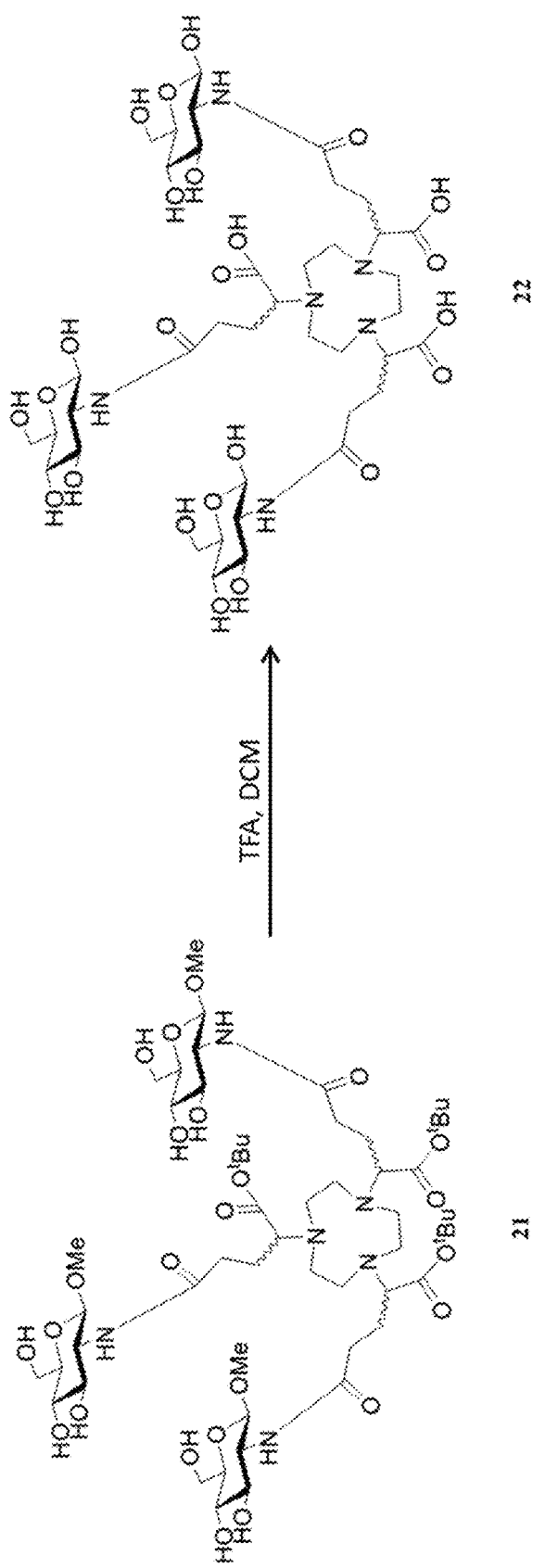

Referring to FIG. 1E, Compound 21 (14 mg) was dissolved in a mixture of trifluoroacetic acid (0.5 ml) and dichloromethane (1 ml), and reacted for 8 hrs at room temperature. The reaction was terminated, and separated by reverse HPLC. The fraction with a retention time of 9.7 min was collected, to obtain Compound 22 (that is, the multivalent saccharide complex NOTA-G3 of the present invention) (2.7 mg, yield 19%). ESI-MS, m/z: 1003.41 [M+H]+, Found 1003.41.

1.2. Synthesis of $^{68}$Ga-NOTA-G3

Figure 2:
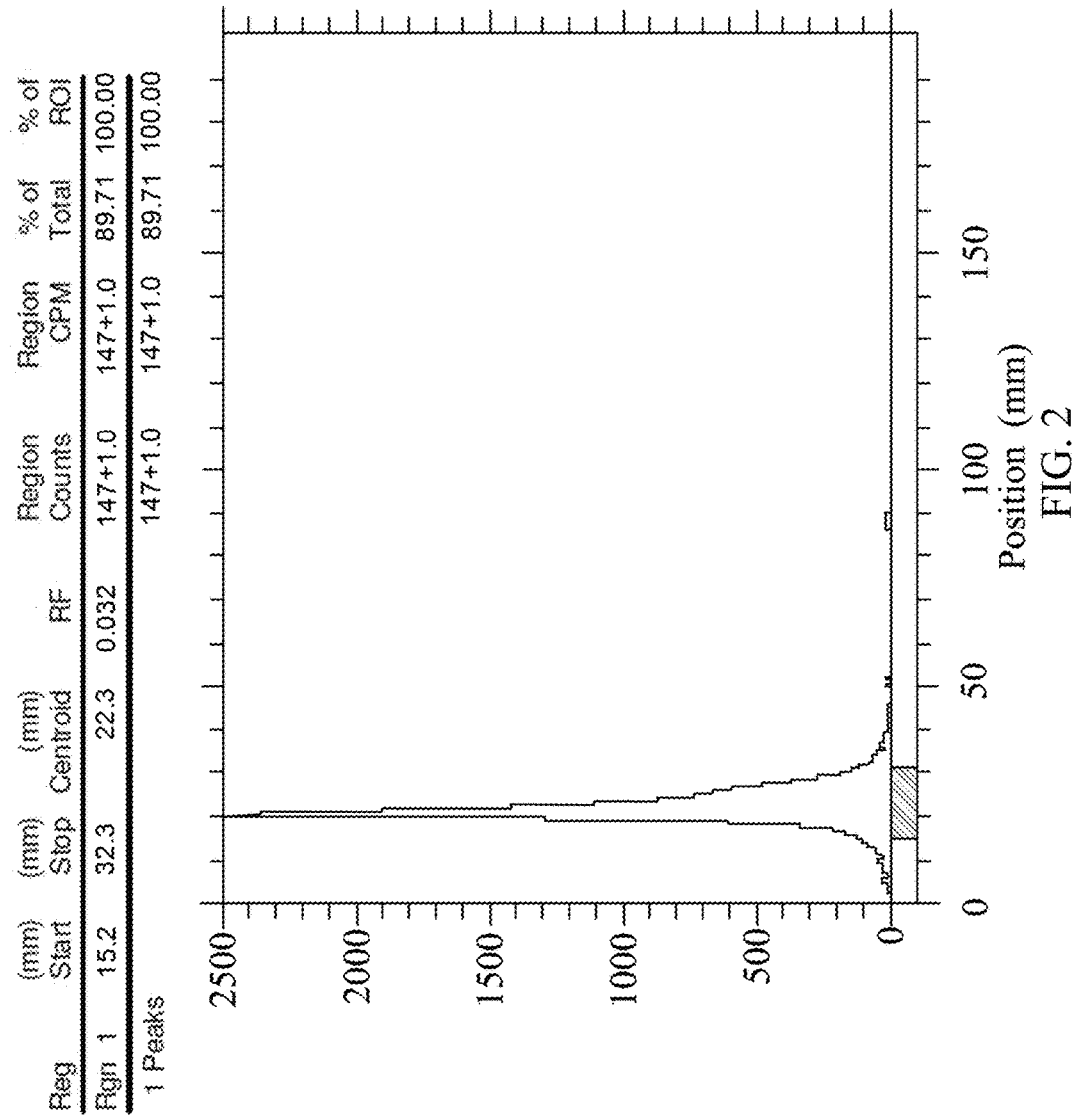
FIG. 2 is an image detected by a radio-TLC imaging scanner of $^{68}$Ga-NOTA-G3 according to an embodiment of the present invention.
Figure 3:
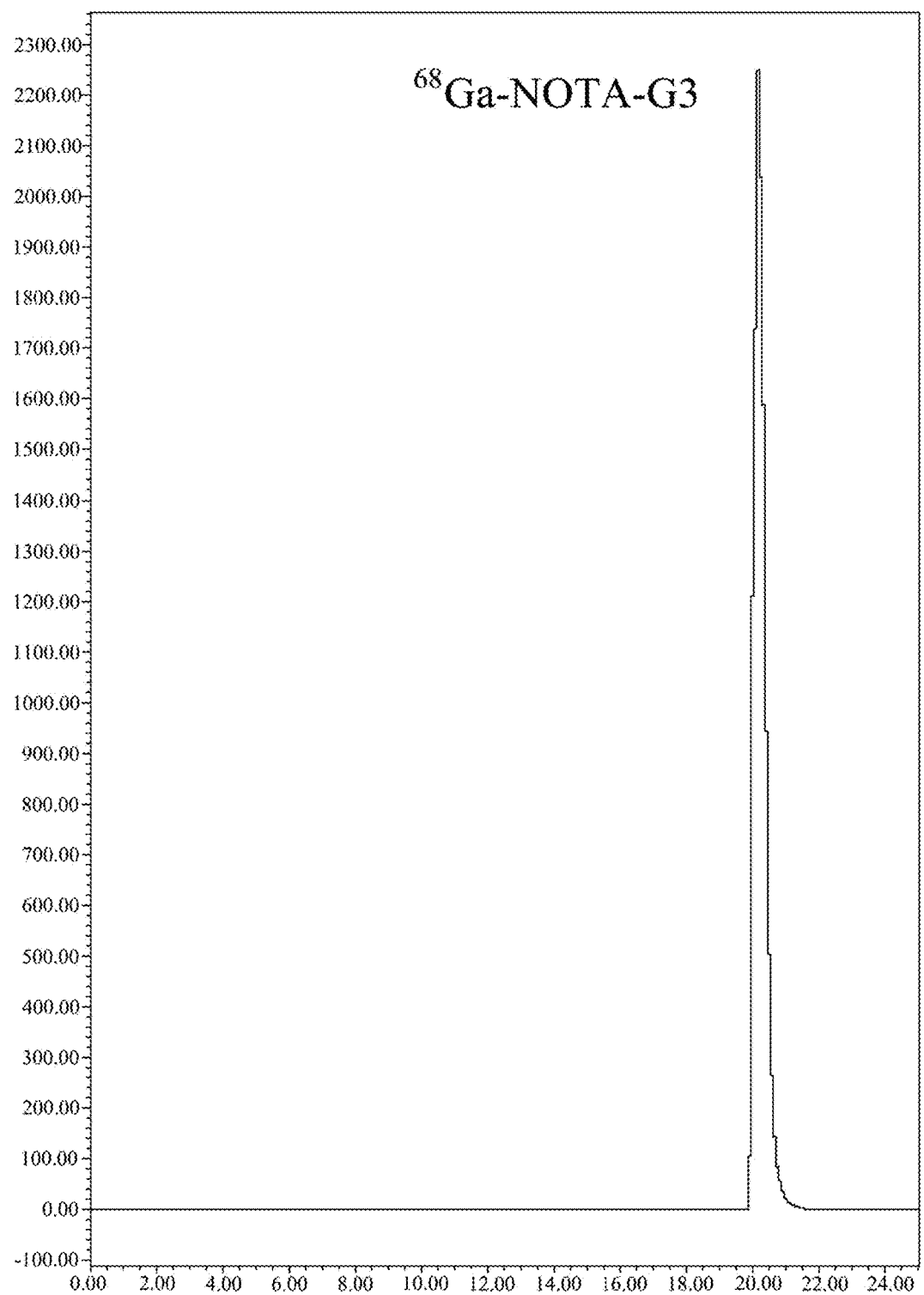
FIG. 3 is a radio-HPLC chromatograph of $^{68}$Ga-NOTA-G3 according to an embodiment of the present invention.

A $^{68}$Ge/$^{68}$Ga generator was panned with 0.1N HCl, to obtain a $^{68}$GaCl$_3$ solution. Then, $^{68}$Ga (0.5 mL, ~185 MBq) and 1M HEPES buffer (0.15 mL) were added to NOTA-G3 (1 μg), and reacted for 15 min at room temperature. The radiochemical purity (RCP) was measured by radio-TLC and radio-HPLC. The results are respectively shown in FIGS. 2 and 3. The RCP of $^{68}$Ga-NOTA-G3 is >95%.

EXAMPLE 2

Evaluation of the Efficacy of the Multivalent Saccharide Complex Labeled with a Radioactive Isotope of the Present Invention in an Animal Model of Lung Cancer In this experimental example, the multivalent saccharide complex $^{68}$Ga-NOTA-G3 prepared in Example 1 and an animal model of NCI-H292 human lung cancer cells, were used to evaluate the efficacy of the multivalent saccharide complex of the present invention.

Figure 4:
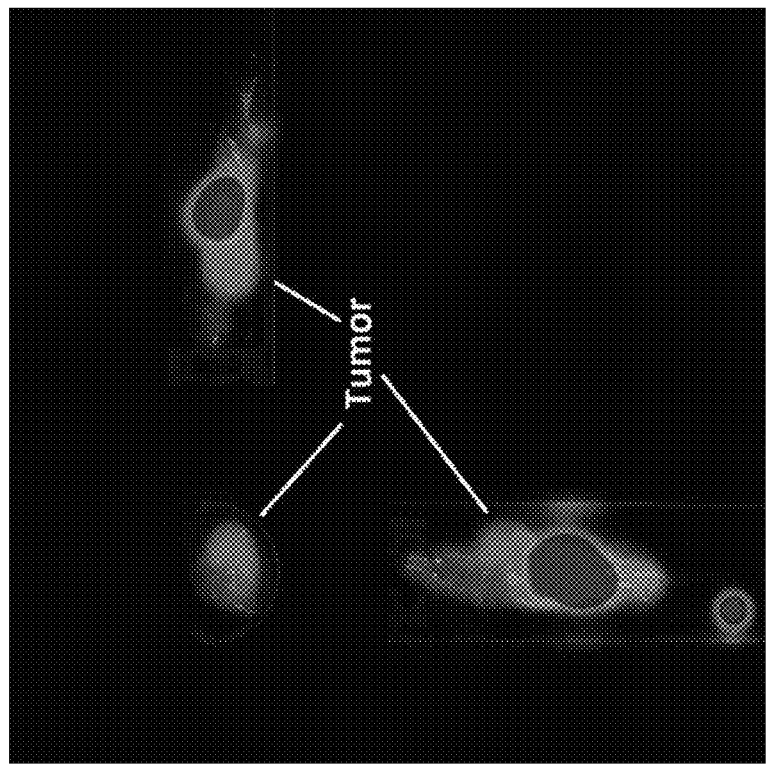
FIG. 4 is a NanoPET/CT image of a multivalent saccharide complex $^{68}$Ga-NOTA-G3 according to an embodiment of the present invention in an animal model of lung cancer.
Figure 5:
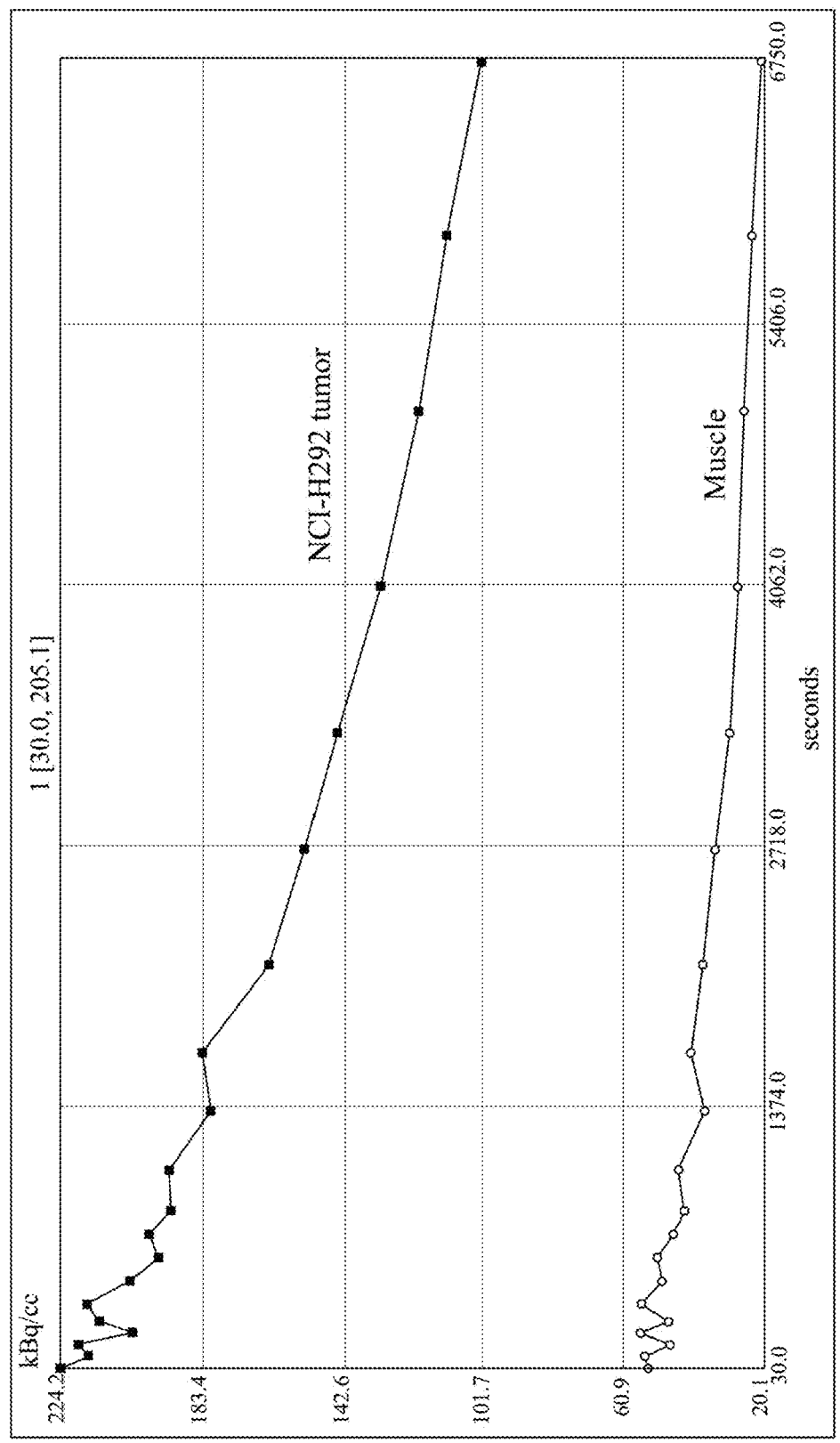
FIGS. 5 and 6 respectively show in-vivo distribution of $^{68}$Ga-NOTA-G3 according to an embodiment of the present invention.
Figure 6:
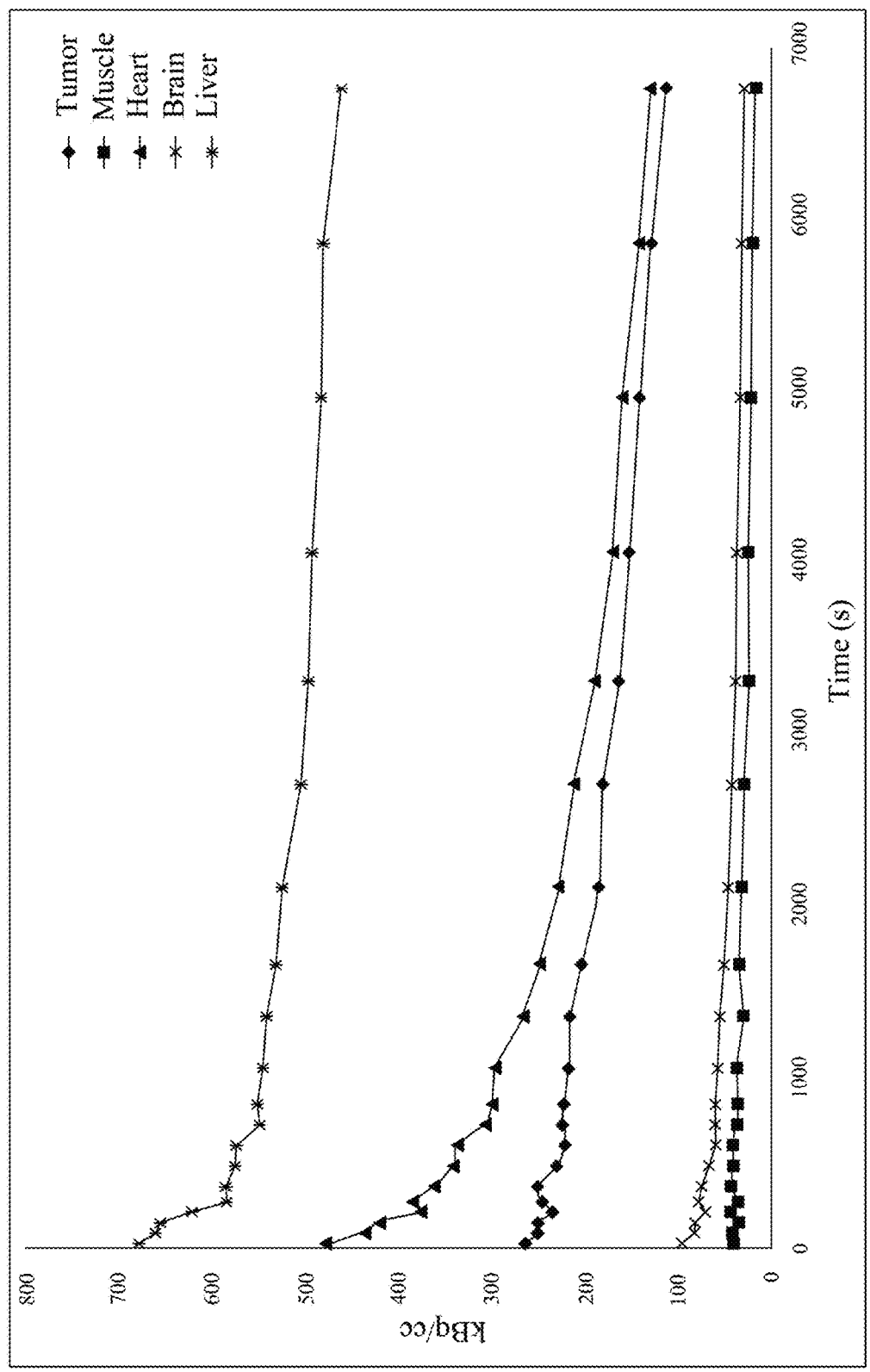

The multivalent saccharide complex $^{68}$Ga-NOTA-G3 (11.1 MBq, dissolved in 0.1 mL saline) was injected to nude mice having NCI-H292 human lung cancer cells at the tail vein. The mice were anesthetized with 1.5% isoflurane, and then imaged by nanoPET/CT. After 2 hrs of dynamic imaging, the result shows that the multivalent saccharide complex $^{68}$Ga-NOTA-G3 is significantly accumulated in the tumor sites with a tumor/muscle ratio of 5.1, indicating that the lung cancer cells are able to effectively take in the $^{68}$Ga-NOTA-G3, as shown in FIG. 4. The time-activity curves generated in the tumor and muscle regions circled in the PET image also show that the activity uptake in the tumor was significantly higher than in the muscle tissue within 2 hrs of imaging, as shown in FIG. 5. The analysis results also show that there was no higher uptake in the brain and heart, as shown in FIG. 6. Thus, it can be seen that the multivalent saccharide complex of the present invention is able to be specifically accumulated in tumors and is effective in enhancing the uptake in tumor.

The specific examples disclosed above are not intended to limit the scope of the claims of the present invention, and modifications may be made by those skilled in the art based on their general knowledge without departing from the principle and spirit of the present invention. Therefore, the scope claimed by the present invention is as defined by the claims of the present invention.

What is claimed is:

1. A multivalent saccharide complex, comprising:
   a chelator, which is 1,4,7-triazacyclononane-N,N',N"-triacetic acid (NOTA), 1,4,7,10-tetraazacyclododecane-1,4,7,10-tetraacetic acid (DOTA), diethylenetriaminepentaacetic acid (DTPA), 1,4,8,11-tetraazacyclotetradecane-N,N', N",N"'-tetraacetic acid (TETA), or 1,4,7-triazacyclononane phosphinic acid (TRAP);
   at least two molecules of a linker, one end of which is attached to the chelator, wherein the linker is polyethylene glycol (PEG), an amino acid, or a peptide; and
   at least two molecules of glucose, attached respectively to the other end of the linker.

2. The multivalent saccharide complex according to claim 1, having a structure of Formula (1):

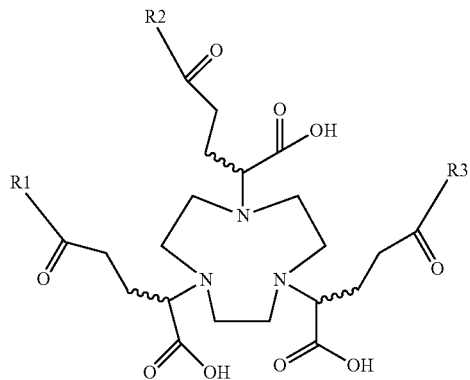

wherein any two functional groups of R1, R2, and R3 are glucosamine, and the other functional group is hydrogen, and wherein the wavy lines ∿ are the molecules of the linker.

3. The multivalent saccharide complex according to claim 2, wherein R1, R2 and R3 are all glucosamine.

4. The multivalent saccharide complex according to claim 2, further comprising a radioactive isotope labeled on the compound of Formula (1).

5. The multivalent saccharide complex according to claim 4, wherein the radioactive isotope is rhenium-188, technetium-99 m, indium-111, lutetium-177, gallium-68, yttrium 90, flurine-18, or copper-64.

6. The multivalent saccharide complex according to claim 4, wherein the radioactive isotope is gallium-68.

7. A contrast agent, comprising:
   a multivalent saccharide complex according to claim 1; and
   an excipient acceptable in the contrast agent.

8. A method for diagnosing cancers, comprising administering an effective amount of a multivalent saccharide complex according to claim 4 to a subject and imaging the subject by nanoPET/CT.

9. The method according to claim 8, wherein the cancers are selected from the group consisting of lymphoma, multiple myeloma, testicular cancer, thyroid cancer, prostate cancer, throat cancer, cervix cancer, nasopharyngeal carcinoma, breast cancer, colorectal cancer, pancreatic cancer, gastric cancer, head and neck cancer, esophageal cancer, rectal cancer, bladder cancer, kidney cancer, lung cancer, liver cancer, brain cancer, melanoma, and skin cancer.

* * * * *